(12) United States Patent
Kosaka

(10) Patent No.: US 6,319,721 B1
(45) Date of Patent: Nov. 20, 2001

(54) METHOD FOR MEASURING TRACE AMOUNT OF PROTEIN

(75) Inventor: Hideko Kosaka, Kyoto (JP)

(73) Assignee: Kyoto Daiichi Kagaku Co., Ltd., Kyoto (JP)

(*) Notice: Subject to any disclaimer, the term of this patent is extended or adjusted under 35 U.S.C. 154(b) by 0 days.

(21) Appl. No.: 09/471,283

(22) Filed: Dec. 23, 1999

(30) Foreign Application Priority Data

Dec. 25, 1998 (JP) .................................................. 10-378426

(51) Int. Cl.[7] .................................................. G01N 33/48
(52) U.S. Cl. .............................. 436/86; 436/164; 436/163; 436/815
(58) Field of Search .............................. 436/86, 164, 163, 436/815

(56) References Cited

U.S. PATENT DOCUMENTS

| 5,399,498 | 3/1995 | Pugia . |
| 5,925,570 | * 7/1999 | Nishidate et al. ...................... 436/74 |

FOREIGN PATENT DOCUMENTS

| 0 345 582 A2 | 12/1989 | (EP) . |
| 1068715 | 5/1967 | (GB) . |
| 4-53265 | 8/1992 | (JP) . |
| 6-70632 | 9/1994 | (JP) . |

OTHER PUBLICATIONS

Fujita, Yoshikazu et al, "Color Reaction Between Pyrogallol Red–Molybdenum(VI) Complex and Protein" Bunseki Kagaku, vol. 32, pp. E379–E386, 1983.

Watanabe *et al.*, "Urinary Protein as Measured with a Pyrogallol Red–Molybdate Complex, Manually and in a Hitachi 726 Automated Analyser," *Clinical Chemistry*, vol. 32, No. 8 (1986), pp. 1551–1554.

* cited by examiner

*Primary Examiner*—Jill Warden
*Assistant Examiner*—Monique T. Cole
(74) *Attorney, Agent, or Firm*—Sughrue, Mion, Zinn, Macpeak & Seas, PLLC

(57) ABSTRACT

A method capable of showing a color change sufficient for indicating the presence and/or concentration of a protein in a protein-containing liquid sample by contacting with the sample, comprising: indium or an induim compound, and a dye or pigment capable of forming a complex with indium.

9 Claims, 2 Drawing Sheets

METHOD FOR MEASURING TRACE AMOUNT OF PROTEIN

BACKGROUND OF THE INVENTION

1. Filed of the Invention

The present invention relates to a composition for detecting or quantifying a protein in a protein-containing liquid sample (e.g., urine) at a low concentration to a trace amount.

2. Brief Description of the Background Art

It is clinically important to judge whether or not a person excessively excretes a protein, such as albumin or the like, into urine. Even in a healthy person, namely a case in which the kidney is normally functioning, an extremely small amount of a protein is excreted and the total amount thereof becomes from 50 to 100 mg per day. Additionally, it is known that the excreted amount increases after physical exercise or depending on the physical conditions, which is generally called physiological proteinuria. According to electrophoresis analyses, about 60% of the proteins excreted into urine of a healthy person is originated from the blood plasma, and albumin having a molecular weight of about 67,000 occupies about 70 to 80% thereof.

In addition to the physiological proteinuria, symptomatic proteinuria is classified into prerenal, renal and postrenal types, and the renal type is further classified into subtypes, such as glomerular origin, tubular origin, and the like. The prerenal proteinuria is a result of leakage of increased blood protein into urine caused by a functional change or disorder of specific organ tissues, and detection of such a specific component is directly connected with morbid state diagnoses. Its typical example is Bence Jones protein which is a tumor marker. Among the renal proteinuria types, the glomerular proteinuria exemplified by albumin and the like is caused by the reduced filtration function of renal glomerular basement membrane, and the tubular protein exemplified by $\beta_2$-microglobulin and $\alpha_1$-microglobulin is caused by the reduced renal tubular re-absorption ability, and both cases can be used as excellent markers for understanding the degree of renal function reduction and renal disorders. The postrenal proteinuria is a proteinuria which is expressed by, for example, bleeding, calculus, tumors, and the like, in certain organs, such as renal pelvis, urinary duct, bladder, urethra, prostate, and the like, and is used for the diagnoses of the above-described topical diseases.

Among a number of proteinuria measuring method, a protein error method using tetrabromophenol blue (TBPB) which is a pH indicator has a long history and is still established as a screening inspection method. TBPB develops yellow color in a solution of pH 2 to 3, and blue color at pH 4 or more, but becomes blue even at pH 3 when a protein is present in the solution. When a test paper, such as filter paper or the like, is impregnated with TBPB together with a buffer of pH 3 making use of this phenomenon, the tone of blue color changes depending on the existing amount of a protein, such as albumin or the like, in urine, so that the degree of proteinuria can be read out from the color tone.

However, generally, this "protein error method" cannot detect a protein of 10 to 15 mg/dl or less. Furthermore, since the method is a test paper method, the detection is out-put qualitatively, such as "−" to "±" to "+". Additionally, the detectable protein is generally only albumin, and globulin which occupies about 40% of plasma proteins, the above-described Bence Jones protein and the like cannot be detected.

In addition to such a qualitative measuring method, there are a number of known methods by which a protein per se can be detected quantitatively. For about 20 years, nephelometry exemplified by the Kingsbury-Clark method has been carried out as a main routine inspection method, but it has problems in that it can hardly react with proteins other than albumin similar to the case of the protein error method. Furthermore, since the method is a manual method, it takes time and labor for the measurement.

A dye binding method using a complex of a dye exemplified by pyrogallol red with a metal, such as molybdenum or the like, is now used most frequently as a quantitative determination method. According to this method, highly accurate measuring results can be obtained not only by manual handling but also by applying it to an automatic analyzer.

JP-B-4-53265 (the term "JP-B" as used herein means an "examined Japanese patent publication") discloses a colorimetric method for the determination of a trace protein, using a dye capable of forming a complex with molybdenum and of shifting its wavelength in the presence of a protein. The basic principle of this method is well known, and, when a substance which binds to molybdenum is present in a test sample, the test shows a negative value in the case of normal urine so that the absorbance becomes lower than that of the measurement of pure water.

For this point, JP-B-4-53265 takes a measure for covering molybdenum in the reagent from inhibiting substances, such as formulation of a chelating agent which binds to molybdenum or formulation of a metal ion which binds to an inhibiting substance, such as citric acid or the like, that binds to molybdenum, in advance in the reagent composition.

Also, JP-B-6-70632 discloses a colorimetric method for the determination of a trace protein, comprising using a polyhydroxybenzene sulfonphthalein dye and/or a polyhydroxybenzene phthalein dye, capable of forming a complex with tungsten and of shifting its wavelength in the presence of a protein, and a buffer for keeping the composition at an acidic pH.

Additionally, a publication "Color Reaction Between Pyrogallol Red-Molybdenum(VI) Complex and Protein", Y. Fujita, I. Mori and S. Kitano, Analytical Chemistry, 32, pp. E379-E386 (1983), describes results of screening tests of metals and dyes, which can be used as a trace protein measuring method making use of the protein error phenomenon. The dye is a polyhydroxybenzene sulfonphthalein dye or a polyhydroxybenzene phthalein dye. Examples of the metals to be screened include molybdenum(VI), bismuth (III), aluminum(III), iron(III), uranium(VI), zirconium(IV), antimony(III), tungsten(VI), cerium(III), tin(IV), zinc(II), manganese(II), mercury(II), silver(I), and cadmium(II)

SUMMARY OF THE INVENTION

An object of the present invention is to detect or quantify a trace protein in a liquid sample, such as urine or the like, by a novel means.

This and other objects of the present invention have been attained by a composition capable of showing a color change sufficient for indicating the presence and/or concentration of a protein in a protein-containing liquid sample by contacting with the sample, comprising:

indium or an indium compound, and a dye or pigment capable of forming a complex with indium.

DETAILED DESCRIPTION OF THE INVENTION

Figure 1:
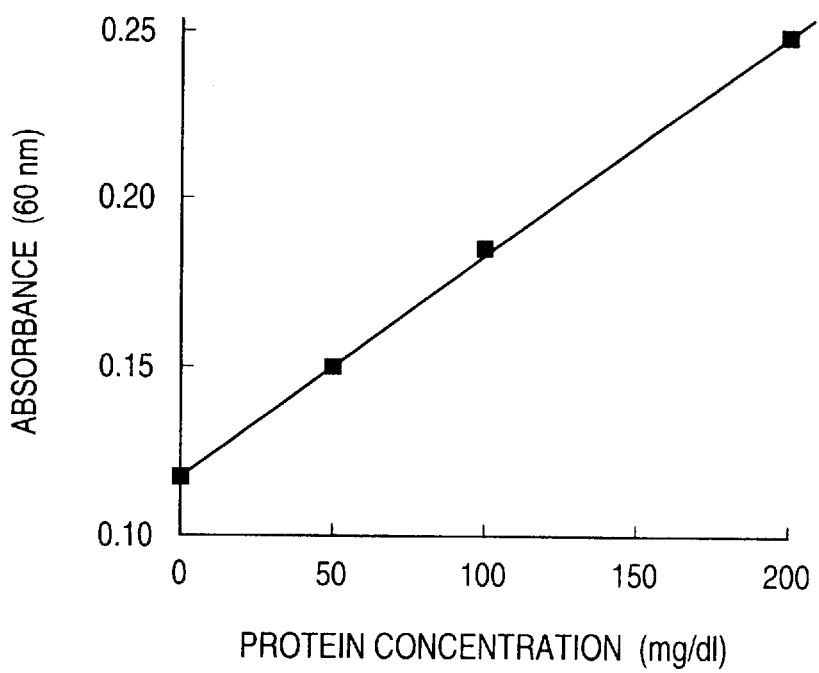
FIG. 1 is a graph showing a result of the measurement of absorbance of serial dilutions of a standard protein solution using the composition of the present invention.

According to the present invention, a protein in a test sample solution can be measured at a low level of from a low concentration to a trace amount using an indicator reagent composition containing a newly improved indium compound/dye or pigment complex, so that it becomes possible to obtain sufficient sensitivity for a protein at such a low level and to judge changes in color tone visually sufficiently. Specifically, a protein in a small to trace amount can be measured, and a protein level of from 0 mg/dl to about 2,000 mg/dl, particularly from 0 mg/dl to about 30 mg/dl, in urine can be measured quantitatively. Additionally, using the reagent composition of the present invention, a urine protein at a level of from a low concentration to a trace amount, such as between 0 mg/dl and about 30 mg/dl, between 0 mg/dl and about 5 mg/dl or between about 5 mg/dl and about 10 mg/dl, can be detected and measured. In the same manner, such an amount of a protein in a spinal fluid can be measured.

The reagent composition of the present invention is suited for the measurement under wet conditions as a liquid reagent and also under dry conditions in which the reagent composition is uniformly incorporated into a carrier. Examples of the carrier for the dry conditions include water-absorbable porous materials such as filter paper, non-water-absorbable materials such as a membrane made of a permeable polymer, and kneaded materials of water-soluble polymers. The reagent composition is included in the carrier uniformly over its entire portion at such a predetermined concentration that a liquid sample can penetrated into the carrier.

Different from the case of JP-B-4-53265, it is not necessary to formulate a chelating agent in advance in the reagent composition for the purpose of covering indium from inhibiting substances or to formulate metal ions, because citric acid or the like which binds to molybdenum is not an inhibiting substance for indium.

The present invention uses a phenomenon in which a polyhydroxybenzene sulfonphthalein dye or a polyhydroxybenzene phthalein dye, such as pyrocatechol violet, pyrogallol red, bromopyrogallol red, xylenol orange, pyrogallol phthalein, o-hydroxyhydroquinone phthalein, or the like, forms a complex with indium and the thus formed complex binds to a protein to shift the wavelength. They may be used alone or as a combination thereof. The composition obtained by the present invention can be used as a liquid system test reagent or processed into a simple dry system test piece.

The indium compound for use in the indium/dye or pigment complex is not particularly limited. However, the indium compound should be sufficiently soluble in water for the purpose of forming a complex with the above-described polyhydroxybenzene sulfonphthalein dye or polyhydroxybenzene phthalein dye. Additionally, it is preferred that the cation of the indium compound for use in the present invention is substantially not colored, in order to avoid interference of the measurement by cations having a high coloring degree. Examples of the indium compound having sufficient solubility in water for forming a complex with the polyhydroxybenzene sulfonphthalein dye or the polyhydroxybenzene phthalein dye include indium sulfate, indium chloride, indium bromide, indium nitrate, and ammonium indium bissulfate. They may be used alone or as a combination thereof.

In a liquid system using the reagent composition of the present invention, the amounts of indium and a dye or pigment capable of forming a complex with indium in the reagent composition are preferably 10 to 400 $\mu$M and 10 to 250 $\mu$M, respectively, and the molar ratio of indium and the dye or pigment is preferably either 1:10 to 1:1 or 5:1 to 1:1. On the other hand, in a dry system, the above range of the amounts and molar ratio can be applied; however, the amounts may be higher.

Any buffers can be used in the present invention, so long as they can keep the reagent reaction system at a constant pH which is sufficient for generating changes in color tone required as an indicator reagent composition and that it can substantially remove changes in color tone caused by the fluctuation of pH of a protein-containing sample to be measured. However, the properties of the buffer change depending on the indium compound/dye or pigment complex mixed in the indicator reagent composition. On the other hand, the amount of the buffer depends on the properties of each sample to be measured. In general, the amount of the buffer in the reagent composition is between about 100 mM and about 500 mM.

Although it is preferred to use a buffer in the reagent composition, it is not always necessary to add the buffer thereto. For example, its effect may be obtained by firstly preparing a composition solely composed of indium or an indium compound and a dye or pigment capable of forming a complex with indium, allowing the reagent composition to contact with a sample to be measured and then adding a buffer which can keep the reaction system at an acidic pH. That is, it includes also a case in which a buffer is added to urine in advance and a case in which a sample to be measured already contains an appropriate amount of an appropriate buffering substance.

Examples of the acidic buffer which can be used in the present invention include a glycine buffer (e.g., glycine/hydrochloric acid), lactate, phthalate, succinate, trichloroacetate, sulfosalicylate, phosphates, acetates, sodium chloride/hydrochloric acid, piperazine-N,N'-bis(2-hydroxypropane)sulfonic acid (POPSO), N-2-hydroxyethylpiperazine-N'-2-ethanesulfonic acid (HEPES), 3-N-(trishydroxymethyl)methylamino-2-hydroxypropanesulfonic acid (TAPSO), and 2-((tris-(hydroxymethyl)methyl)amino)ethanesulfonic acid (TES), and other acidic buffers which are well known in the art and can keep a pH value of preferably from 2.0 to 4.0, more preferably from 2.2 to 2.7.

The reagent composition of the present invention may also contain an optional component such as a surfactant which does not substantially change the properties and functions of the indium compound/dye or pigment complex and buffer and does not interfere the protein measurement. In addition to the possibility of increasing the reactivity with the protein by the addition of a surfactant, the addition of a surfactant (though limited to a liquid system reagent solution conditions) has an effect to prevent staining of the inside of the reaction cell. The surfactant may be either a nonionic surfactant or an anionic surfactant suitably. Also, the amount of the surfactant in the reagent composition is preferably about 0.001 to 1% by weight.

Suitable examples of the nonionic surfactant include Triton series, methyl cellulose, polyvinyl alcohol, and Brij series. Suitable examples of the anionic surfactant include sodium lauryl sulfate, sodium laurylbenzene sulfonate, and polyacrylic acid.

Examples of other unimportant components in the same manner include a polymer compound, a plasticizer, and a dyestuff which is used as an inert base.

Additionally, JP-B-6-70632 describes that chelating agents are not contained in the reagent and that, on the contrary, chelating agents interfere the measurement when they are contained. However, according to other important feature of the present invention, the composition of the present invention functions smoothly even if chelating agents are contained. For example, the measurement does not cause incorrect results even if the reagent or urine contains a compound having chelating action, such as a glycine buffer, tartaric acid, oxalic acid, citric acid, iminodiacetic acid (IDA), or the like.

The present invention can be applied to a dry type test piece which can be obtained in accordance with a general dry test piece preparation method. For example, it can be prepared by impregnating a piece of a water-absorbable porous material such as filter paper with an aqueous solution of the reagent composition of the present invention, drying the piece and then optionally pasting it on a water-non-permeable material to be used as a handhold.

A trace protein in a liquid sample can be quantified according to the method of the present invention by showing a color change sufficient for indicating the presence and/or concentration of the protein in the sample.

Examples of the present invention are given below by way of illustration and not by way of limitation.

EXAMPLE 1

A reagent solution having the following composition was prepared by dissolving reagents of the following formulation in purified water.

| | |
|---|---|
| Bromopyrogallol red (DOJINDO LABORATORIES) | 0.05 mM |
| Indium sulfate (NAKALAI TESQUE, INC.) | 0.05 mM |
| Succinate buffer (succinic acid + sodium hydroxide) | pH 2.7 |
| Sodium lauryl sulfate (NAKALAI TESQUE, INC.) | 0.1% |

As a standard protein solution, human serum albumin was adjusted to 200 mg/dl. Using this standard solution, serial dilutions having respective concentrations shown in the abscissa of FIG. 1 were prepared. The reagent solution (350 $\mu$l) was added to 5 $\mu$l of each of the thus prepared samples, and the mixture was incubated at 37° C. for 10 minutes to measure an absorbance at 600 nm. The results are shown in FIG. 1. As can be understood from the drawing, a markedly excellent calibration curve was obtained.

EXAMPLE 2

Figure 2:
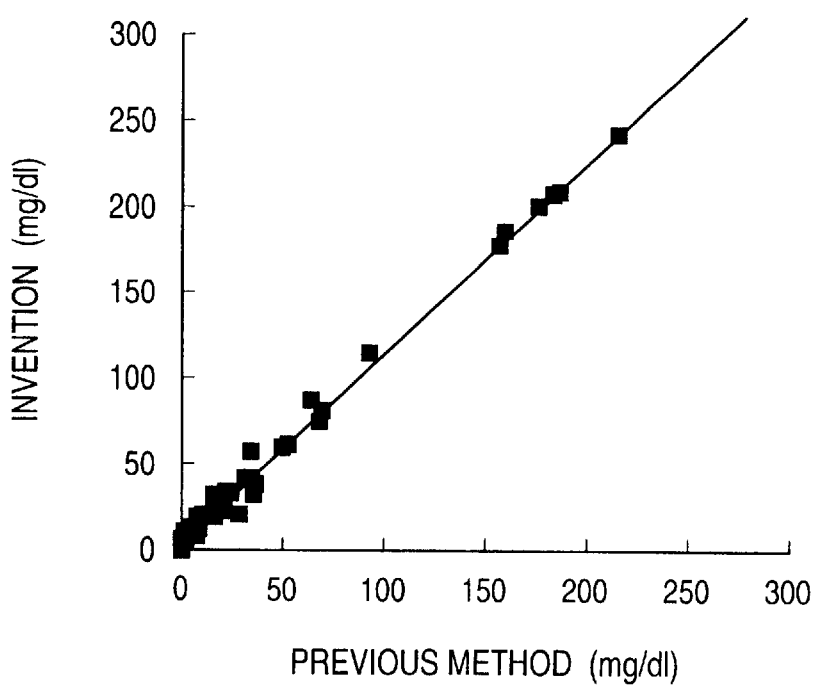
FIG. 2 is a graph showing correlation between the composition of the present invention and a previous method.

A total of 60 urine samples from patients were measured by the same procedure of Example 1. The measurement was also carried out by a previous method (pyrogallol red-molybdenum method; commercial reagents) to examine correlation between the inventive method and the previous method. The results are shown in FIG. 2. Markedly excellent correlation was obtained with a correlation coefficient of 0.9946.

EXAMPLE 3

A reagent solution having the following composition was prepared by dissolving reagents of the following formulation in purified water, a sheet of filter paper (manufactured by Whatman Corp.: 3MMchr) was impregnated with the reagent solution, pulled up from the solution and blast-dried at 50° C. for 10 minutes, and then the thus obtained base sheet was cut into a strip of 5 mm×80 mm to be used as a dry test paper.

| | |
|---|---|
| Bromopyrogallol red (NAKALAI TESQUE, INC.) | 0.25 mM |
| Indium sulfate (NAKALAI TESQUE, INC.) | 0.25 mM |
| Succinate buffer (succinic acid + sodium hydroxide) | pH 2.7 |
| Triton x-100 (NAKALAI TESQUE, INC.) | 0.5% |

The standard protein solution (10 $\mu$l) having a concentration shown in Table 1 was spotted on the thus obtained dry test paper, and change in color tone on the spot was observed with the naked eye 30 seconds thereafter. As shown in Table 1, it was able to judge the results sufficiently with the naked eye.

TABLE 1

| Protein Concentration (mg/dl) | Observed Color |
|---|---|
| 0 | Pink |
| 10 | Red violet |
| 30 | Violet |
| 100 | Blue violet |

EXAMPLE 4

A regent solution having the following composition was prepared by dissolving reagents of the following formulation in purified water.

| | |
|---|---|
| Bromopyrogallol red (DOJINDO LABORATORIES) | 0.05 mM |
| Indium sulfate (NAKALAI TESQUE, INC.) | 0.05 mM |
| Glycine buffer (glycine + hydrochloric acid) | pH 2.2 |
| Polyacrylic acid (WAKO PURE CHEMICAL INDUSTRIES, LTD.) | 0.1% |
| Iminodiacetic acid (DOJINDO LABORATORIES),Citric acid (NAKALAI TESQUE, INC.) or Tartaric acid (NAKALAI TESQUE, INC.) | 0.1% |

Figure 3:
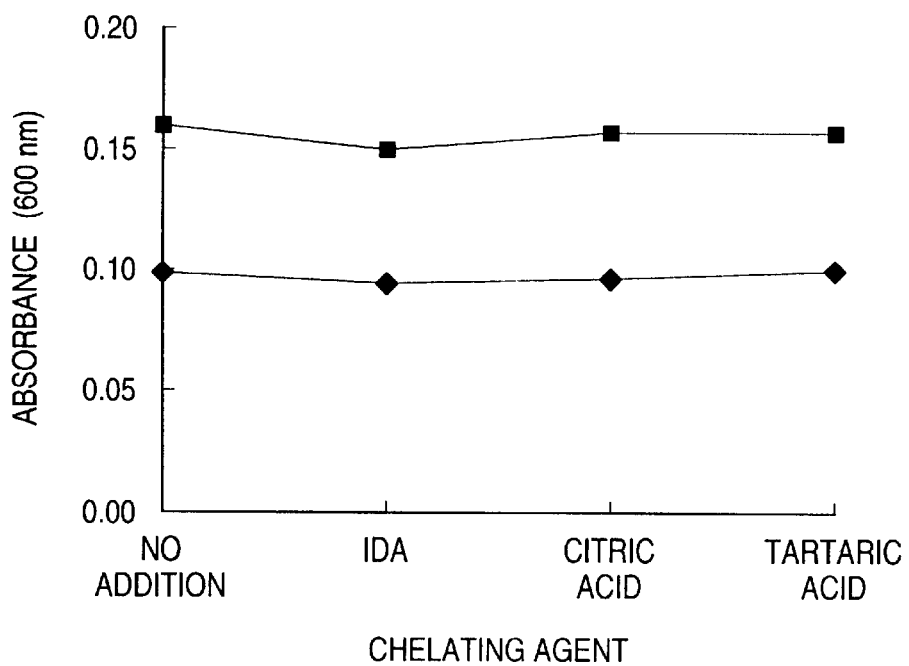
FIG. 3 is a graph showing a result of absorbance measurement when a chelating agent is added to the composition of the present invention.

The reagent solution (350 $\mu$l) was added to 5 $\mu$l of a urine sample which had been prepared by adding 100 mg/dl of human serum albumin to normal pooled human urine, and the mixture was incubated at 37° C. for 10 minutes to measure an absorbance at 600 nm. The results are shown in FIG. 3. In FIG. 3, the symbol "♦" represents the normal pooled human urine samples, and the symbol "■" represents the urine samples which had been prepared by adding 100 mg/dl of human serum albumin to normal pooled human urine. As can be understood from the drawing, fluctuation of measured values did not occur when chelating agents were present in the reagent.

EXAMPLE 5

A reagent solution having the following composition was prepared by dissolving reagents of the following formulation in water.

| | |
|---|---|
| Bromopyrogallol red (DOJINDO LABORATORIES) | 0.05 mM |
| Indium sulfate (NAKALAI TESQUE, INC.) | 0.05 mM |
| Succinate buffer (succinic acid + sodium hydroxide) | pH 2.7 |
| Polyacrylic acid (WAKO PURE CHEMICAL INDUSTRIES, LTD.) | 0.1% |

Figure 4:
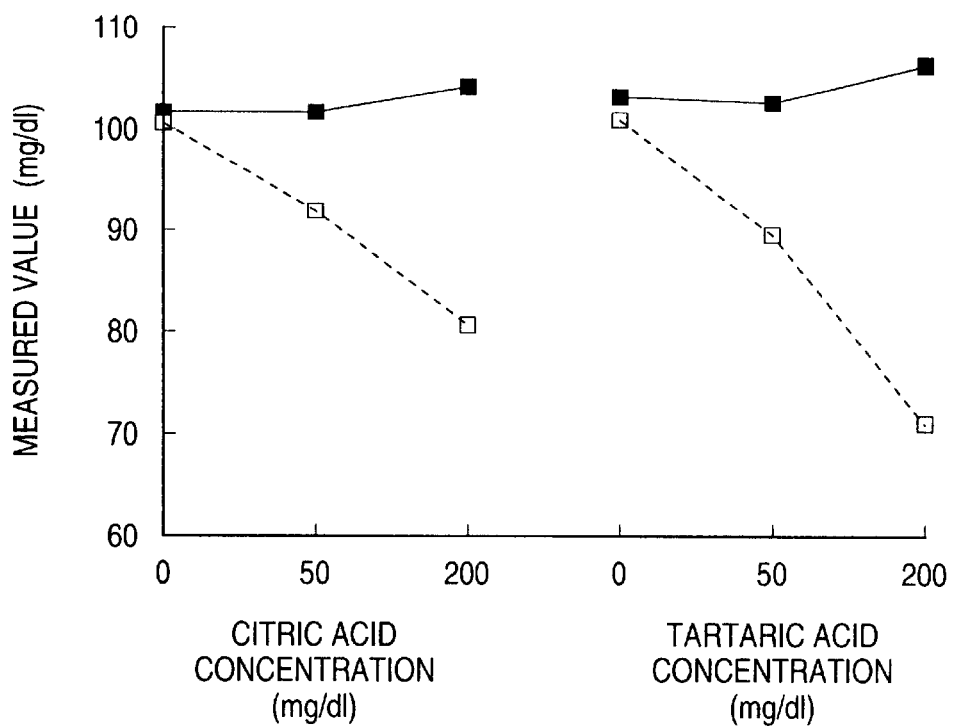
FIG. 4 is a graph showing comparison of the composition of the present invention with a previous method when a chelating agent is added.

Samples were prepared by adding 0, 50 or 200 mg/dl of citric acid or tartaric acid as a chelating agent to a urine sample which had been prepared by adding 100 mg/dl of human serum albumin to normal pooled human urine. The reagent solution (350 μl) was added to 5 μl of each of the thus prepared samples, and the mixture was incubated at 37° C. for 10 minutes to measure an absorbance at 600 nm. The measurement was also carried out by a previous method (pyrogallol red-molybdenum method). The results are shown in FIG. 4. In FIG. 4, the symbol "■" represents the samples measured by the method of the present invention, and the symbol "□" represents the samples measured by the previous method. When chelating agents were present in the samples, fluctuation of measured values occurred by the previous method but did not occur when the composition of the present invention was used.

While the invention has been described in detail and with reference to specific examples thereof, it will be apparent to one skilled in the art that various changes and modifications can be made therein without departing from the spirit and scope thereof.

The priority application, Japanese patent application No. Hei 10-378426, filed Dec. 25, 1998, is incorporated herein by reference in its entirety.

What is claimed is:

1. A method for detecting or quantifying a protein in a sample, comprising
    contacting the sample with a composition capable of showing a color change sufficient for indicating the presence and/or concentration of a protein in a protein-containing liquid sample,
    wherein said composition comprises:
        indium or an indium compound, and
        a dye or pigment capable of forming a complex with indium.

2. The method according to claim 1, wherein the sample contains a buffer for keeping the composition at an acidic pH.

3. The composition according to claim 1, wherein the method contains a buffer for keeping the composition at an acidic pH.

4. The method according to claim 1, wherein the dye or pigment is at least one selected from the group consisting of a polyhydroxybenzene sulfonphthalein dye and a polyhydroxybenzene phthalein dye.

5. The method according to claim 1, wherein the dye or pigment is at least one selected from the group consisting of pyrocatechol violet, pyrogallol red, bromopyrogallol red, xylenol orange, pyrogallol phthalein, and o-hydroxyhydroquinone phthalein.

6. The method according to claim 1, wherein the buffer is at least one selected from the group consisting of lactate, phthalate, succinate, trichloroacetate, sulfosalicylate, phosphates, acetates, sodium chloride/hydrochloric acid, glycine/hydrochloric acid, piperazine-N,N'-bis(2-hydroxypropane)sulfonic acid (POPSO), N-2-hydroxyethylpiperazine-N'-2-ethanesulfonic acid (HEPES), 3-N-(trishydroxymethyl)methylamino-2-hydroxypropanesulfonic acid (TAPSO), and 2-((tris-(hydroxymethyl)methyl)amino)ethanesulfonic acid (TES).

7. The method according to claim 1, which further comprises a surfactant.

8. The method according to claim 1, wherein the sample is urine.

9. The method according to claim 1, wherein the indium compound is at least one selected from the group consisting of indium sulfate, indium chloride, indium bromide, indium nitrate, and ammonium indium bissulfate.

* * * * *